US007794436B2

(12) United States Patent
Pinel

(10) Patent No.: US 7,794,436 B2
(45) Date of Patent: Sep. 14, 2010

(54) CONTROLLED GASTRIC BOLUS FEEDING DEVICE

(76) Inventor: Lloyd Jay Pinel, P.O. Box 442, Silverado, CA (US) 92676

( * ) Notice: Subject to any disclaimer, the term of this patent is extended or adjusted under 35 U.S.C. 154(b) by 1317 days.

(21) Appl. No.: 10/866,006

(22) Filed: Jun. 12, 2004

(65) Prior Publication Data

US 2005/0154357 A1 Jul. 14, 2005

Related U.S. Application Data

(63) Continuation-in-part of application No. 10/755,992, filed on Jan. 13, 2004, now abandoned.

(51) Int. Cl.
*A61M 5/00* (2006.01)

(52) U.S. Cl. .................... 604/247; 604/246; 604/93.01

(58) Field of Classification Search .................. 604/80, 604/246–248, 122, 45, 256, 258, 85, 30–44, 604/77–79, 48, 19, 93.01; 215/11.1, 11.4, 215/11.5, 902
See application file for complete search history.

(56) References Cited

U.S. PATENT DOCUMENTS 2,850,211 A * 9/1958 Fernandez .................. 222/67
2,999,499 A 9/1961 Willet
3,216,419 A * 11/1965 Scislowicz .................. 604/127
3,929,157 A * 12/1975 Serur ......................... 137/453
4,043,332 A * 8/1977 Metcalf ...................... 604/141
4,062,360 A * 12/1977 Bentley ...................... 604/541
4,096,879 A * 6/1978 Serur et al. ................. 137/391
4,405,316 A 9/1983 Mittleman
4,425,123 A * 1/1984 Di Salvo ..................... 604/247
4,464,175 A * 8/1984 Altman et al. ........... 604/99.01
4,474,574 A * 10/1984 Wolfe et al. .................. 604/85
4,515,588 A * 5/1985 Amendolia ................. 604/118
4,534,758 A * 8/1985 Akers et al. .................. 604/85
4,573,631 A * 3/1986 Reeves ....................... 229/404
4,588,396 A * 5/1986 Stroebel et al. ............ 604/246
4,687,473 A * 8/1987 Raines ....................... 604/251
4,725,268 A * 2/1988 Ostensen et al. ........... 604/323
4,735,606 A * 4/1988 Davison ....................... 604/28
4,735,607 A * 4/1988 Keith, Jr. .................... 604/540
4,822,339 A * 4/1989 Tran ............................ 604/82
4,858,619 A * 8/1989 Toth ........................... 600/561
4,863,429 A * 9/1989 Baldwin ..................... 604/135

(Continued)

*Primary Examiner*—Kevin C Sirmons
*Assistant Examiner*—Michael J Anderson
(74) *Attorney, Agent, or Firm*—Robert T. Braun; Claye E. Gaetje

(57) ABSTRACT

A gravity bolus feeding device having a cylindrical body with and intake valve to control or prevent flow of fluid through the feeding device. The device also has a check valve to receive fluids expelled from the patient back into the feeding device. The check valve allows such fluids to rejoin the fluid path and be re-fed to the patient, while allowing air to vent. A burp baffle for use with this or another feeding device to prevent spillage or splashing, while taking in or venting air. The burp baffle has a bottom section which snugly fits into the device, with a notch or opening near its outer periphery, allowing fluid to pass. A center section connected to the bottom section allows fluid to flow around it and into an opening generally opposite the notch. A top section covers the feeding device, and has a hole that allows fluid to vent out the top of the feeding device.

14 Claims, 5 Drawing Sheets

U.S. PATENT DOCUMENTS 4,898,581 A * 2/1990 Iwatschenko ............... 604/122
4,925,444 A * 5/1990 Orkin et al. ................... 604/80
4,941,875 A * 7/1990 Brennan ...................... 604/81
4,944,732 A * 7/1990 Russo ........................ 604/247
4,950,254 A * 8/1990 Andersen et al. ............ 604/247
5,059,173 A * 10/1991 Sacco .......................... 604/80
5,073,166 A * 12/1991 Parks et al. ................. 604/175
5,114,412 A * 5/1992 Flinchbaugh ............... 604/247
5,116,316 A * 5/1992 Sertic et al. ................... 604/83
5,460,603 A * 10/1995 DeSantis ..................... 604/30
5,484,405 A * 1/1996 Edstrom, Sr. ................ 604/77
5,562,638 A * 10/1996 Severs ........................ 604/266
5,575,779 A * 11/1996 Barry ......................... 604/246
5,599,303 A * 2/1997 Melker et al. ................. 604/80
5,707,356 A * 1/1998 Paul ........................... 604/119
5,730,730 A * 3/1998 Darling, Jr. ................. 604/246
5,935,100 A * 8/1999 Myers ......................... 604/81
6,017,332 A * 1/2000 Urrutia ....................... 604/254
6,059,747 A * 5/2000 Bruggeman et al. ......... 604/500
6,083,204 A * 7/2000 Malerba et al. ............. 604/181
6,106,503 A * 8/2000 Pfeiderer et al. ............ 604/246
6,126,632 A * 10/2000 Verbovszky et al. .......... 604/78
6,213,986 B1 * 4/2001 Darling, Jr. ................. 604/248
6,261,267 B1 * 7/2001 Chen .......................... 604/247
6,379,340 B1 * 4/2002 Zinger et al. ................ 604/246
6,482,170 B1 11/2002 Andersen
6,558,346 B1 * 5/2003 Yoshioka et al. .............. 604/67
6,620,141 B2 * 9/2003 Levell ........................ 604/319
6,641,562 B1 * 11/2003 Peterson ..................... 604/141
6,673,051 B2 * 1/2004 Flinchbaugh ............... 604/247
6,691,924 B1 * 2/2004 Vestergaard et al. ...... 236/92 B
6,981,967 B2 * 1/2006 Massengale et al. ........ 604/174
7,001,365 B2 * 2/2006 Makkink .................... 604/254
7,185,782 B2 * 3/2007 Vilchez et al. .............. 220/506
2002/0107490 A1 * 8/2002 Butterfield et al. .......... 604/247
2002/0143318 A1 * 10/2002 Flinchbaugh ............... 604/544
2004/0059287 A1 * 3/2004 Vest et al. ..................... 604/80
2004/0254542 A1 * 12/2004 Sacco ......................... 604/247
2005/0154356 A1 * 7/2005 Pinel .......................... 604/247
2006/0122576 A1 * 6/2006 Raja et al. ................ 604/890.1

* cited by examiner

FIG. 4
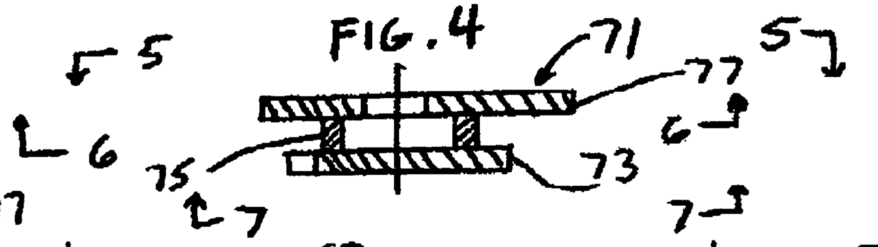
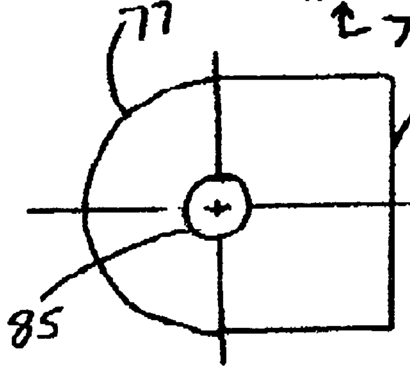
FIG. 5
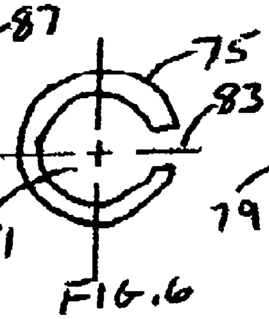
FIG. 6
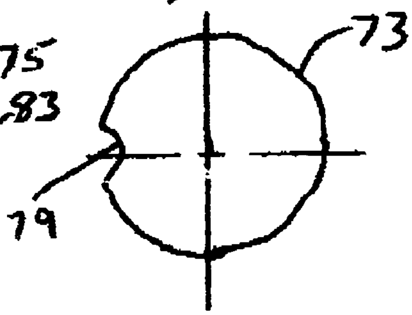
FIG. 7
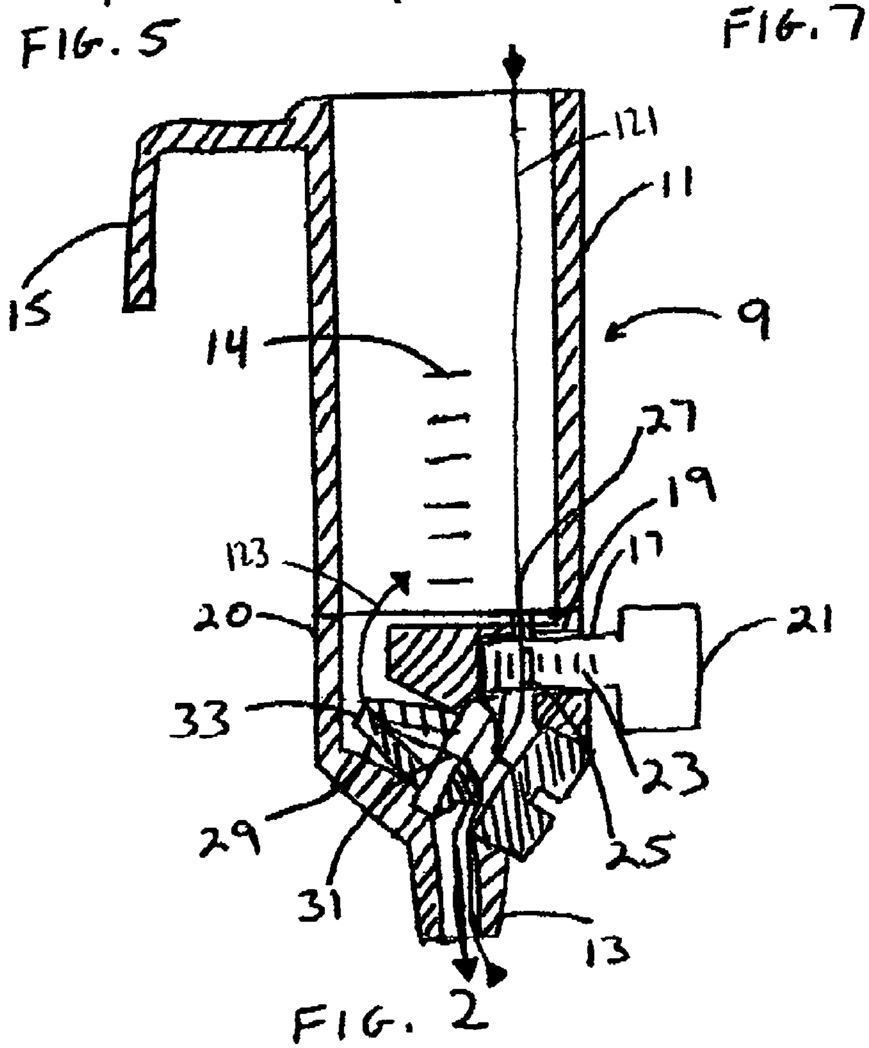
FIG. 2

FIG. 8
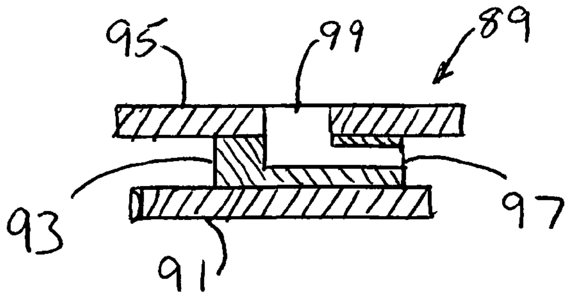
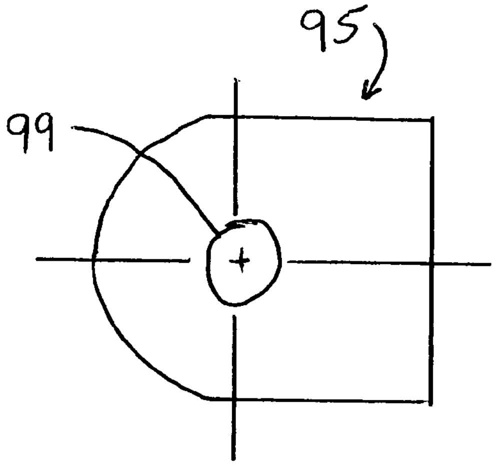
FIG. 9
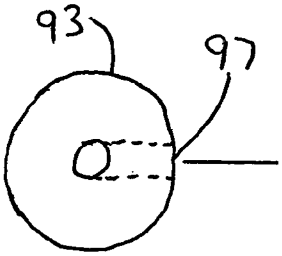
FIG. 10
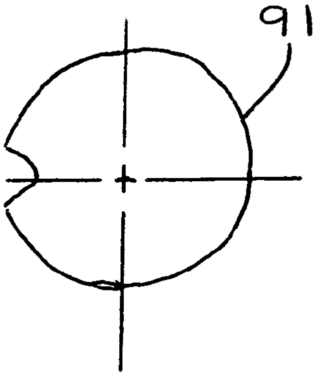
FIG. 11

CONTROLLED GASTRIC BOLUS FEEDING DEVICE

RELATED APPLICATION DATA

This application is a continuation-in-part of U.S. patent application Ser. No. 10/755,992, filed Jan. 13, 2004, now abandoned entitled Controlled Gastric Bolus Feeder.

BACKGROUND OF THE INVENTION

1. Field of the Invention

This patent relates to the feeding of persons with gastric feeding tubes, and more particularly to gravity bolus feeding devices for use in the feeding of such persons.

2. Summary of Related Art

For persons with gastric feeding tubes, there are three common methods for feeding:

1. Gravity feeding with an intravenous-type bag and tubing;
2. Utilizing a feeding pump with bag and tubing; and
3. Gravity bolus feeding.

The first two methods are commonly used in the hospital setting. For many persons with gastric feeding tubes, it is important to be able to vent air and stomach contents back up the gastric tube during and after a feeding. Methods 1 and 2 above can benefit from the device described in U.S. Pat. No. 6,482,170.

Gravity bolus feeding is the primary method for out-of-hospital feeding. Typically, gravity bolus feeding uses a syringe barrel connected to the gastric feeding tube. The syringe barrel is filled with liquid food. To control the rate of feeding, the syringe barrel is raised or lowered by hand. The open tube allows air and stomach contents to vent back into the syringe barrel.

This method suffers from a number of disadvantages:

(a) A person must hold the syringe barrel for the entire twenty to forty minutes a typical feeding takes.

(b) Holding the syringe barrel too high results in too rapid of a feeding, which can cause reflux of the stomach contents and possible aspiration.

(c) Holding the syringe barrel too low causes the liquid food to return to the syringe barrel, which increases feeding time.

(d) Once the feeding is started, it is difficult to interrupt or stop if necessary.

(e) When venting occurs, the contents of the syringe barrel are often splashed out of the open top.

(f) The typical syringe barrel only holds 60 cubic centimeters of liquid food, much less than the average of approximately 200 cubic centimeters that many adults require for a feeding.

(g) The flow of liquid food can only be stopped by clamping the gastric feeding tube, which also prevents venting back into the syringe barrel.

SUMMARY OF THE INVENTION

In accordance with the present invention, there is provided a gravity bolus feeding device for use with a gastric feeding tube. The feeding device has a cylindrical body, with an intake valve and a check valve. The intake valve controls the rate of flow of liquid food from the cylindrical body, and can stop the flow if desired. The check valve allows venting of air and stomach contents back into the cylindrical body from the person's stomach. The check valve remains operational even when the intake valve is closed.

The intake valve and check valve combine to minimize splashing of liquid food when the person burps or otherwise vents stomach contents and air back through the gastric feeding tube into the feeding device. The check valve returns the air and stomach contents into the cylindrical body. The air vents through the top, if necessary, and the stomach contents remain in the cylindrical body to be re-fed to the person.

The feeding device also can have an adjustable handle adapted to fit over a crib rail or chair back, allowing a person to divert their attention without interrupting the feeding. Additionally, a hanger can be added to the handle to hang the device over a hook or peg, or from an I.V. pole.

A burp baffle is adapted to cover the top of the feeding device. The burp baffle allows venting of air, while preventing the splashing of liquid food out the top of the feeding device. Additionally, the burp baffle has a flat edge that allows the feeding device to be laid down or rested on it, to prevent rolling or spilling.

The burp baffle has a bottom portion, a center portion, and a top portion. The top portion covers the top of the feeding device, and the bottom portion fits snugly within the feeding device. Both the bottom portion and the top portion have a hole, notch, or other opening. The center portion connects the two, and provides a fluid path that connects the two holes, notches, or other openings. This connection allows air to vent or be taken in, and further prevents liquid food from splashing or spilling out.

It is an object of the present invention to provide a gravity bolus feeding device with a more precise method for controlling flow of liquid food. The present invention provides an intake valve that allows the flow of liquid food to be controlled or stopped.

It is an object of the present invention to provide a gravity bolus feeding device that allows interruption of the liquid flow while still allowing venting of the stomach contents back into the device. The present invention provides an intake valve to prevent liquid flow, without interrupting the operation of the check valve, which allows venting of the stomach contents back into the device.

It is an object of the present invention to provide a gravity bolus feeding device that allows a caregiver to divert their attention without interrupting the feeding. The present invention provides a handle and additionally a hanger to allow the feeding device to remain upright and operational when the caregiver must attend to other needs.

It is an object of the present invention to provide a gravity bolus feeding device that minimizes or prevents splashing of the liquid food in the device when stomach contents are vented back into the device. The present invention provides an intake valve and a check valve, which together cooperate to minimize splashing of the liquid food.

It is an object of the present invention to prevent splashing or spilling of the liquid food when stomach contents are vented back into the device. The present invention provides a burp baffle to cover the top of a feeding device, preventing splashing. The openings, notches, channels, and cavities in the burp baffle are situated to prevent spilling of the liquid food.

It is an object of the present invention to allow venting or intake of air from the top of a gravity bolus feeding device without allowing liquid food to splash or spill out. The present invention provides a burp baffle with a series of openings, notches, channels, and cavities to allow air to flow in and out as necessary. The configuration of the openings, notches, channels, and cavities is such that liquid cannot easily spill out.

The above, as well as other advantages of the present invention, will become readily apparent to those skilled in the art from the following detailed description of a preferred embodiment when considered in the light of the accompanying drawings.

BRIEF DESCRIPTION OF THE DRAWINGS

FIG. 2 is a cross-sectional drawing of one embodiment of a gravity bolus feeding device.

FIG. 4 is a cross-sectional drawing of a burp baffle.

FIG. 5 is a top view of a burp baffle, taken along lines 5-5 of FIG. 4.

FIG. 6 is a top view of the center section of a burp baffle, taken along lines 6-6 of FIG. 4.

FIG. 7 is a bottom view of a burp baffle, taken along lines 7-7 of FIG. 4.

FIG. 8 is a drawing of another embodiment of a burp baffle.

FIG. 9 is a top view of the embodiment of a burp baffle shown in FIG. 8.

FIG. 10 is a top view of the center section of the embodiment of the burp baffle shown in FIG. 8.

FIG. 11 is a bottom view of the embodiment of the burp baffle shown in FIG. 8.

DETAILED DESCRIPTION OF THE PREFERRED EMBODIMENT

Figure 1:
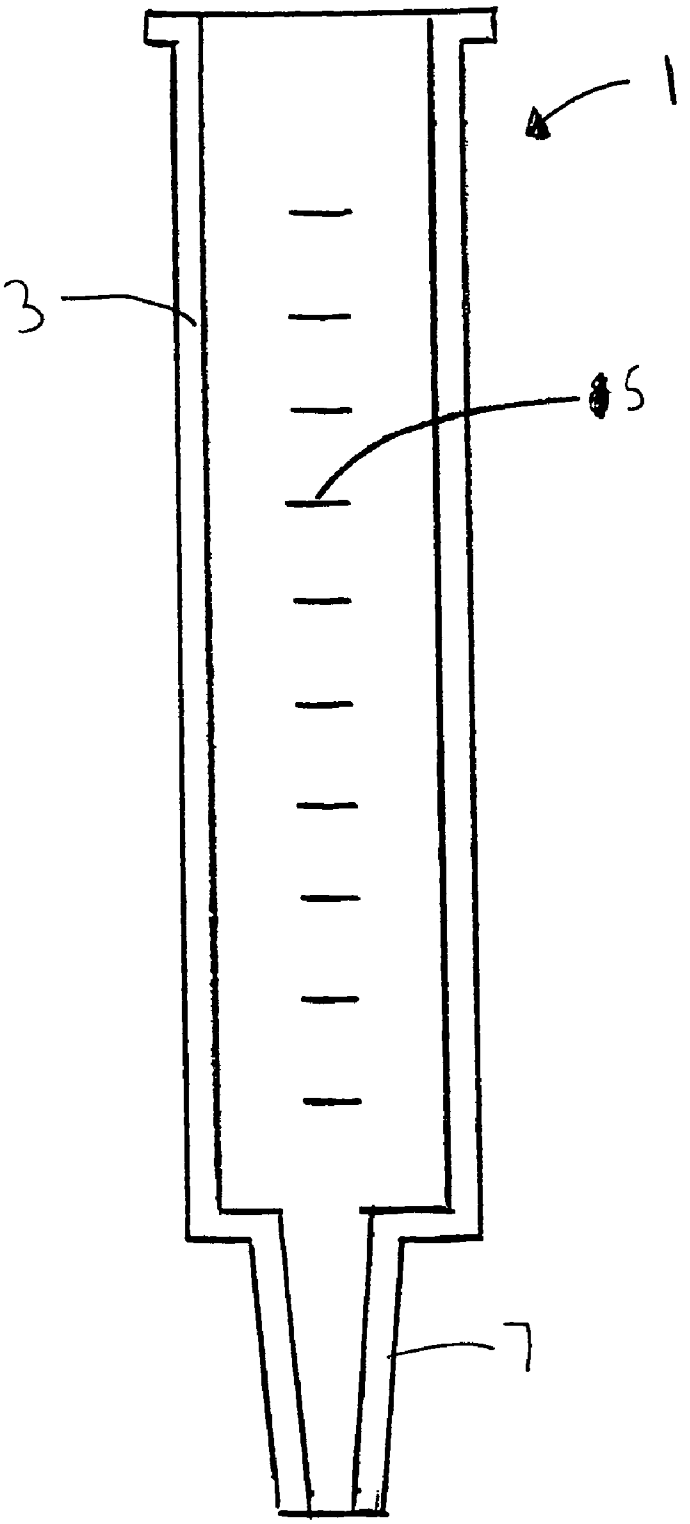
FIG. 1 PRIOR ART
FIG. 1 is a cross-sectional drawing of a syringe barrel.

Referring more particularly to the drawings, FIG. 1 shows a syringe barrel 1. A syringe barrel 1 is the conventional prior art device used for gravity bolus feeding of persons having gastric feeding tubes. The syringe barrel 1 has an elongated cylindrical body 3, and may include quantity markings 5 on the cylindrical body 3 to indicate quantities of liquid within the cylindrical body 3. The cylindrical body 3 has an open top and a tapered bottom tip 7. The tapered bottom tip 7 removably connects to a gastric feeding tube (not shown) to allow gravity to draw liquid from the cylindrical body 3 through the tapered bottom tip 7, and into the gastric feeding tube. Through this method, the person is fed.

Typically, such syringe barrels 1 can hold approximately sixty cubic centimeters of liquid. While this is suitable for some infants, children and adults may on average consume approximately 200 cubic centimeters during 30 minutes of feeding. Therefore, feeding an adult using a syringe barrel 1 could require refilling the syringe barrel 1 three times.

FIG. 2 shows a cross-section drawing of a gravity bolus feeding device 9, according to one embodiment of the invention. This embodiment of the gravity bolus feeding device 9 has an elongated cylindrical body 11 with a bottom tip 13. The bottom tip 13 removably connects to a gastric feeding tube (not shown) to allow gravity to draw liquid from the cylindrical body 11 through the bottom tip 13, and into the gastric feeding tube. The bottom tip 13 may be smooth, but is preferably ribbed to increase the pressure needed to remove it from the gastric feeding tube, thereby preventing accidental or inadvertent removal. Additionally, the bottom tip 13 may preferably be tapered.

The top of the elongated cylindrical body 11 is generally open, but can be covered, without sealing, by the burp baffle shown in FIGS. 4 through 11, to prevent spillage when the feeding device 9 is laid down or otherwise not upright, or when the person burps or otherwise expels stomach contents back into the feeding device 9. The cylindrical body 11 may include quantity markings 14 to indicate the quantities of liquid within the cylindrical body 11. The cylindrical body 11 may also have a handle 15, used to hang the feeding device 9 from a crib rail, chair back, line, or other suitable location such that the feeding device 9 is above the stomach level of the person. Preferably, the handle 15 is either movable or located such that the bottom tip 13 of the feeding device 9 is between approximately twelve and eighteen inches above stomach level.

An intake valve 17 is located in a valve seating 19 near the bottom of the elongated cylindrical body 11. The intake valve 17 may be located on a removable bottom section 20. The removable bottom section 20 may be removed from the main elongated cylindrical body 11 to facilitate cleaning, for example. The intake valve 17 controls flow of liquid from the cylindrical body 11 to the bottom tip 13, and thereafter into the gastric feeding tube. The intake valve 17 is any suitable valve that (1) can prevent liquid of various viscosities from flowing into the bottom tip 13, and (2) can control the flow of such liquids up to a maximum desired feeding rate, on average 200 cubic centimeters in thirty minutes. The intake valve 17 may be controlled manually, mechanically, electrically, electronically, or by any other suitable method.

The intake valve 17 may be controlled by a knob 21 having threads 23. The operator turns the knob 21 and screws the intake valve 17 into or out of the elongated cylindrical body 11. The knob 21 may have markings (not shown) to indicate the openness of the intake valve 17, and thereby the relative flow rate of the liquid out of the elongated cylindrical body 11. Additionally, the markings may be on the elongated cylindrical body 11. The shaft of the intake valve 17 has a hole 25 through it, which either does or does not align with a hole 27 in the valve seating 19 to prevent or control the flow of the liquid, opening or dosing a first fluid path 121 from the elongated cylindrical body 11 to the bottom tip 13.

Seated between the intake valve 17 and the bottom tip 13 is a check valve 29. Preferably, the check valve 29 is a duck-bill check valve, but any one-way valve is suitable. The check valve 29 does not restrict the flow of liquid from the intake valve 17 into the bottom tip 13. However, the check valve 29 is positioned such that the intake valve 17, the valve seating 19, and the check valve 29 entirely close off the elongated cylindrical body 11 from the bottom tip 13.

The check valve 29 has an intake 31 disposed generally toward the bottom tip 13, and an outtake 33 disposed toward the elongated cylindrical body 11. The outtake 33 is positioned such that liquid flowing through the check valve 29 wilt be expelled into the elongated cylindrical body 11 above the intake valve 17. In terms of the first fluid path 121, the liquids would rejoin the first fluid path 121 before the intake valve 17. The check valve 29 defines a second fluid path 123 from the intake 31, through the check valve 29 body, and out through the outtake 33.

In operation, the check valve 29 allows the person to vent both air and stomach contents back into the feeding device 9, as through burping. The pressure caused by such venting opens the check valve 29, and allows air and liquid to pass back into the elongated cylindrical body 11. The air will eventually vent out the top of the feeding device 9, while the liquid will rejoin the first fluid path 121 to continue feeding of the person. Because the intake valve 17, the valve seating 19, and the check valve 29 entirely close off the bottom tip 13 from the elongated cylindrical body 11, pressure is released only through the check valve 29, and splashing of liquid in the elongated cylindrical body 11 is minimized.

Figure 3:
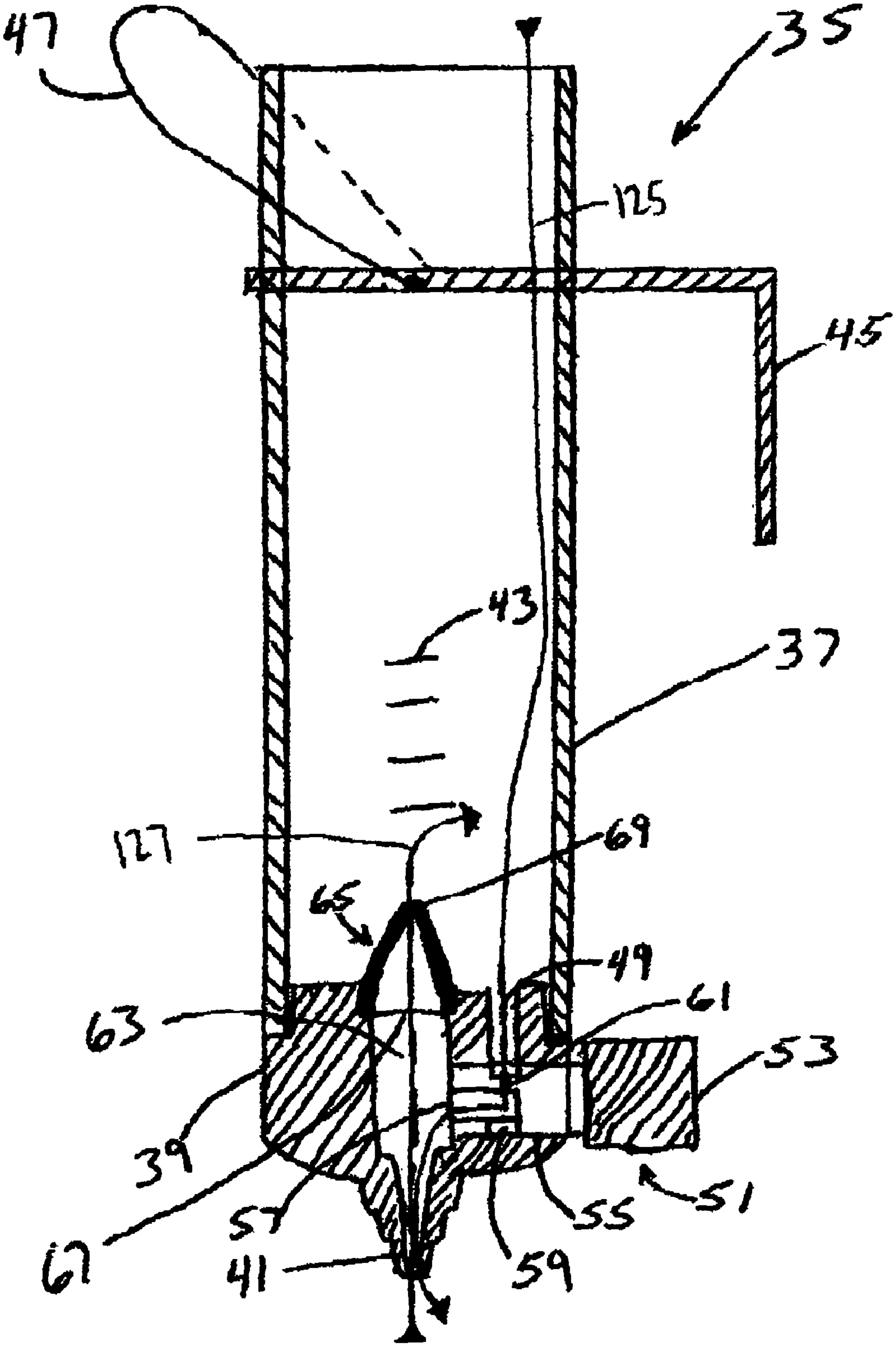
FIG. 3 is a cross-sectional drawing of another embodiment of a gravity bolus feeding device.

Referring now to FIG. 3, there is shown another embodiment of an improved gravity bolus feeding device 35. This embodiment also contains an elongated cylindrical body 37 with a removable bottom portion 39. The removable bottom portion 39 has a bottom tip 41. The bottom tip 41 removably connects to a gastric feeding tube (not shown) to allow gravity to draw liquid from the cylindrical body 37 through the bottom tip 41, and into the gastric feeding tube. The bottom tip 41 may be smooth, but is preferably ribbed to increase the pressure needed to remove it from the gastric feeding tube, thereby preventing accidental or inadvertent removal. Additionally, the bottom tip 41 may preferably be tapered.

The top of the elongated cylindrical body 37 is generally open, but can be covered, without sealing, by the burp baffle shown in FIGS. 4 through 11, to prevent spillage when the feeding device 35 is laid down or otherwise not upright, or when the person burps or otherwise expels stomach contents back into the feeding device 35. The cylindrical body 37 may include quantity markings 43 to indicate the quantities of liquid within the cylindrical body 37. The cylindrical body 37 may also have a handle 45, used to hang the feeding device 35 from a crib rail, chair back, line, or other suitable location such that the feeding device 35 is above the stomach level of the person. Preferably, the handle 45 is either movable or located such that the bottom tip 41 of the feeding device 35 is between approximately twelve and eighteen inches above stomach level. The handle 45 is also preferably movable around the elongated cylindrical body 37 to facilitate different orientations of the feeding device 35. Additionally, a hanger 47 is attached either to the elongated cylindrical body 37 or, more preferably, to the handle 45, to allow hanging from a hook or I.V. pole.

The removable bottom portion 39 can securely attach to the elongated cylindrical body 37 by any method, but preferably the bottom portion 39 is either threadably screwed on, or snugly presses into the elongated cylindrical body 37, sealed with a rubber O-ring. The bottom portion 39 can be removed for cleaning.

The bottom portion 39 contains a hole 49, opening into the elongated cylindrical body 37. The other end of the hole 49 connects to an intake valve 51, which controls flow of liquid from the cylindrical body 37 to the bottom tip 41, and thereafter into the gastric feeding tube. The intake valve 51 is any suitable valve that (1) can prevent liquid of various viscosities from flowing into the bottom tip 41, and (2) can control the flow of such liquids up to a maximum desired feeding rate, approximately 200 cubic centimeters in thirty minutes. The intake valve 51 may be controlled manually, mechanically, electrically, electronically, or by any other suitable method.

The intake valve 51 may be similar to the intake valve 17, described above. Another form of intake valve 51 may be a knob 53 for turning a shaft 55. The shaft 55 has a central bore 57 with one end opening toward the bottom tip 41. The other end of the central bore 57 connects with a lateral hole 59 extending to the circumference of the shaft 55. When the lateral hole 59 is aligned with the hole 49 in the bottom portion 39, flow of liquid is enabled from the elongated cylindrical body 37 into the bottom tip 41. When they are not aligned, flow is prevented.

Preferably, a tapered channel 61 will extend from the lateral hole 59 partially around the shaft 55. The tapered channel 61 will be deepest at the intersection with the lateral hole 59, and will taper shallower until it is coincident with the diameter of the shaft 55. This tapered channel 61 allows further control of the flow rate of liquid from the elongated cylindrical body 37 into the bottom tip 41. When the shallow portion of the tapered channel 61 is aligned with the hole 49 in the bottom portion 39, flow of fluid is less than when the deeper portion of the tapered channel 61 is aligned. Flow of fluid is still greater when the lateral hole 59 is aligned with the hole 49 in the bottom portion 39. The hole 49 in the bottom portion 39, and the intake valve 51 define a first fluid path 125 from the elongated cylindrical body 37 to the bottom tip 41.

The bottom portion 39 contains a second hole 63, opening into the elongated cylindrical body 37. The other end of the second hole 63 opens generally toward the bottom tip 41, and generally into the first fluid path 125 after the intake valve 51. A check valve 65 is seated in the second hole 63. Preferably, the check valve 65 is a duck-bill check valve, but any one-way valve is suitable. The check valve 65 does not restrict the flow of liquid from the intake valve 51 into the bottom tip 41. However, the check valve 65 is positioned such that the intake valve 51, the bottom portion 39, and the check valve 65 entirely close off the elongated cylindrical body 37 from the bottom tip 41.

The check valve 65 has an intake 67 disposed generally toward the bottom tip 41, and an outtake 69 disposed toward the elongated cylindrical body 37. The outtake 69 is positioned such that liquid flowing through the check valve 65 will be expelled into the elongated cylindrical body 37 above the intake valve 51. In terms of the first fluid path 125, the liquids would rejoin the first fluid path 125 before the intake valve. The check valve defines a second fluid path 127 from the intake 67, through the check valve 65 body, and out through the outtake 69.

In operation, the check valve 65 allows the person to vent both air and stomach contents back into the feeding device 35, for example through burping. The pressure caused by such venting opens the check valve 65, and allows air and liquid to pass back into the elongated cylindrical body 37. The air will eventually vent out the top of the feeding device 35, while the liquid will rejoin the first fluid path 125 to continue feeding of the person. Because the intake valve 51, the bottom portion 39, and the check valve 65 entirely close off the bottom tip 41 from the elongated cylindrical body 37, pressure is released only through the check valve 65, and splashing of liquid in the elongated cylindrical body 37 is minimized. This provides an advantage in those instances when medical personnel need to ensure that the person is fed the entire amount of liquid, for example of some medicines, or to allow the feeder to confirm the actual amount fed. This provides an additional advantage of allowing measurement of the amount of refluxed liquid food after feeding is completed.

Although both the intake valves 17, 51, and the check valves 29, 65, are defined specifically, it will be obvious to one of ordinary skill in the art that any suitable valves can be used in place of the specifically-described valves. Further, the valves are shown in their preferred arrangements, including generally the angles with respect to the elongated cylindrical body 37. However, the valves may be seated in any angle or position that allows proper flow or venting of air or liquid.

Referring now to FIGS. 4 through 7, a burp baffle 71 is shown. The burp baffle 71 is suitable for use with either the prior art syringe barrel 1, or with the improved gravity bolus feeding devices 9, 35, described above. Additionally, the burp baffle 71 is shown with a circular cross-section. However, other shapes can be made that are suitable to accommodate different shapes of feeding devices or barrels. The burp baffle 71 is designed to take in or vent air, and to prevent spillage with the device is laid down or when the person burps.

The burp baffle 71 has a bottom section 73, a center section 75, and a top section 77. The bottom section 73 is generally the same shape and size as the cross-section of the inside of the elongated cylindrical body 37, so as to fit snugly within the elongated cylindrical body 37. As shown more clearly in FIG. 7, the bottom section 73 has a notch 79 or other opening cut into its outer circumference. Although FIG. 7 shows the notch cut at the outer circumference, it is permissible to have a hole near the outer circumference, without actually being at the edge. If gravity or pressure allow, the notch 79 or other opening allows air or liquid to pass from the elongated cylindrical body 37 to the center section 75 of the burp baffle 71.

The center section 75 of the burp baffle 71 is shown in FIGS. 4 and 6. The size of the center section 75 is smaller than the cross-section of the inside of the elongated cylindrical body 37, to allow air and liquid to flow around it. Also, the shape of the center section 75 is preferably the same as the inside of the elongated cylindrical body 37, but is not necessarily so. The center section 75 has a hollow central cavity 81 with an opening 83 generally on the opposite side from the notch 79 in the bottom section 73. It is preferable to have the opening 83 exactly opposite from the notch 79, but the opening 83 can be moved around the circumference without departing from the spirit and scope of the invention. This arrangement requires air or liquid to travel in opposite directions in flowing from the elongated cylindrical body 37 through the bottom section 73 and into the center section 75. This path allows air to exhaust, but makes liquid extremely unlikely to inadvertently enter the center section 75.

The top section 77 of the burp baffle 71 is shown in FIGS. 4 and 5. The top section 77 is larger than the top opening of the elongated cylindrical body 37, to completely cover it. The top section 77 has a hole 85 that lines up with the hollow central cavity 81 of the center section 75. This hole 85 allows air to flow in and out of the burp baffle 71 easily, without allowing liquid to easily escape the feeding device 9, 35. The hole 85 is preferably concentric with the hollow central cavity 81, but this is not required for the invention. Preferably, the top section 77 has at least one flat edge 87, to allow the feeding device 9, 35 to be laid down or leaned on the flat edge 87, without rolling or moving.

Referring now to FIGS. 8 through 11, a second embodiment of a burp baffle 89 is shown. The burp baffle 89 has a bottom section 91, a center section 93, and a top section 95. The bottom section 91 and top section 95 have similar shapes and functions to the corresponding bottom section 91 and top section 95 in the previous embodiment. The center section 93 is slightly different, however.

Instead of having a hollow central cavity 81, the center section 93 in this embodiment has a hollow channel 97 where the opening 83 was in the previous embodiment. This hollow channel 97 connects a hole 99 in the top section 95 with the concentric cavity defined by the bottom section 91, the top section 95, the outside circumference of the center section 93, and the inner wall of the elongated cylindrical body 37. Again, air or liquid are required to travel in opposite directions to flow from the elongated cylindrical body 37 to the center section 93, and out the hole 99 in the top section 95.

Figure 12:
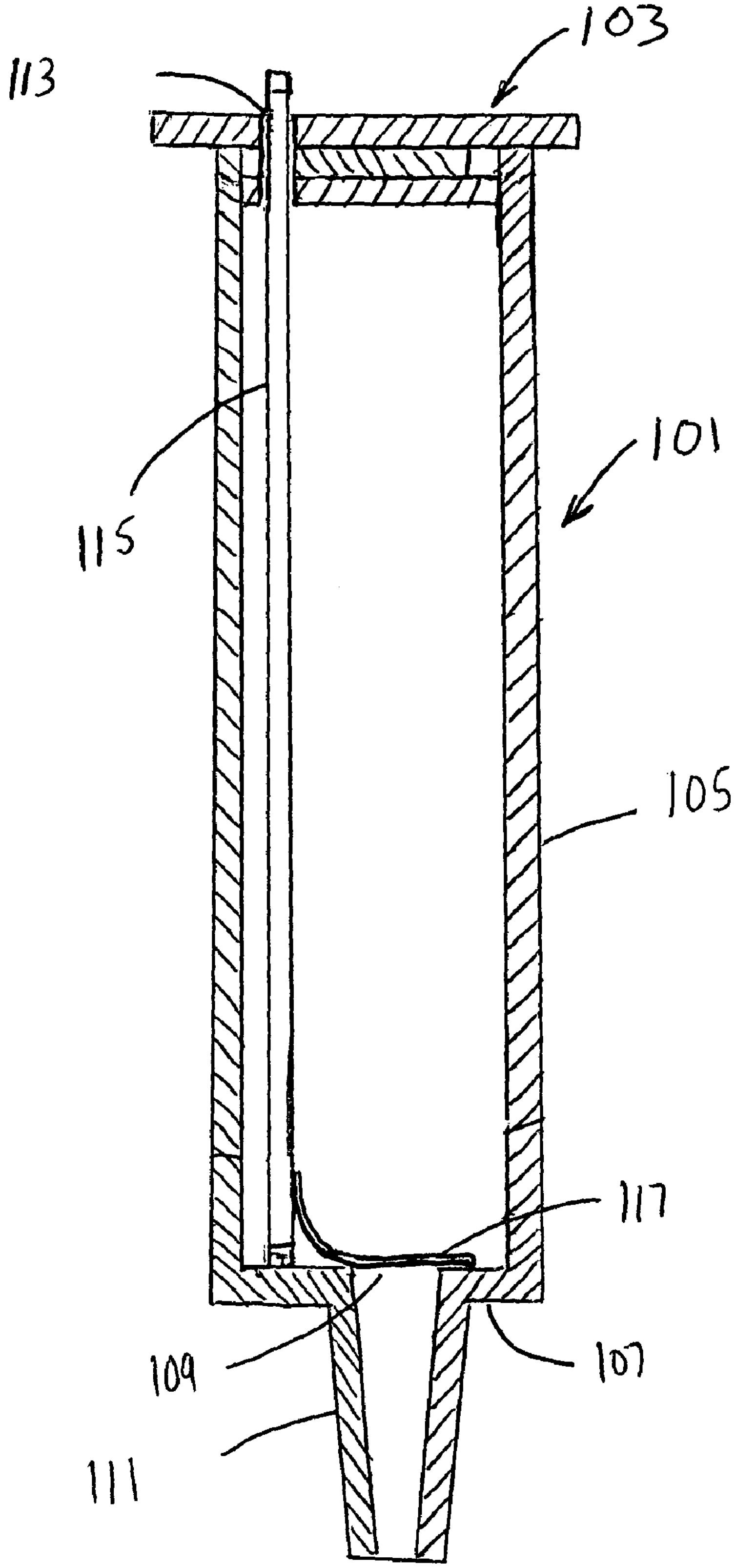
FIG. 12 is a drawing of a combined burp baffle and intake valve.

Referring to FIG. 12, there is shown a combined apparatus 101 comprising a burp baffle 103 and a cylindrical body 105. The cylindrical body 105 has a bottom 107 which is at least partially open. The opening 109 in the bottom 107 connects to a tapered bottom tip 111. Preferably, the opening 109 is slightly off-center from the cylindrical body 105.

The burp baffle 103 is constructed similarly to the above-disclosed burp baffles 71, 89. However, the burp baffle 103 has an additional hole 113 completely through it from top to bottom, substantially parallel to the elongated direction of the cylindrical body 105. The hole 113 does not intersect any of the cavities, holes, channels, notches, or other fluid pathways in the burp baffle 103. Inserted substantially air- and fluid-tight through the hole 113 is a guide rod 115, running substantially the entire length of the cylindrical body 105. The guide rod 115 is attached to the bottom 107 of the cylindrical body 105 by a pin, bump, notch, or other suitable attachment that allows the guide rod 115 to rotate but not slide across the bottom 107.

Attached to the guide rod 115 above the bottom 107 is a foot 117. The foot 117 extends transversely across and toward the bottom 107 of the cylindrical body 105. The foot 117 is positioned such that when the guide rod 115 is rotated to one position, the foot 117 completely covers the opening 109 in the bottom 107, thereby restricting flow of liquid through the opening 109. When the guide rod 115 is rotated to another position, the foot 117 partially or completely uncovers the opening 109, thereby allowing partially restricted or unrestricted flow of liquid through the opening 109.

The foot 117 may be made of a flexible material, such as soft plastic or rubber. This flexibility will allow fluids vented from the stomach to pass through the foot 117 into the cylindrical body 105, even when the foot 117 completely covers the opening 109. In this way, the foot acts similarly to both the intake valve 17, 51, and the check valve 29, 65.

While the burp baffle 103, guide rod 115, and foot 117 are specifically designed to work with a separate cylindrical body 105, the combination is also suitable for use with the syringe barrel 1 of the prior art, or either of the embodiments of the gravity bolus feeding devices 9, 35, disclosed above. These may need to be modified to ensure that the guide rod 115 does not slide when rotated. Also, when used with the gravity bolus feeding devices 9, 35, the foot 117 is positioned to cover the hole 27, 49 at the bottom of the cylindrical body 11, 37.

The feeding device 9, 35, the combined apparatus 101, and the burp baffle 71, 89, 103 may be made of any suitable material. Preferably, with the exception of the valves, the materials are not breakable and are either translucent or transparent. Most preferably, the materials are plastic, although glass, metal, or other watertight materials are acceptable.

Most preferably, the feeding device 9, 35, the combined apparatus 101, and the burp baffle 71, 89, 103 have circular cross-sections. However, the shapes can be altered into other geometric or irregular shapes as necessary or desired, without departing from the invention.

The intake valves 17, 51 may be made of metal, plastic, or any other suitable material. Preferably, stainless steel is used. The check valves 29, 65 are preferably made of plastic or, most preferably, rubber.

Any snug, liquid-tight, or other removable connection may be made by any appropriate connecting method. Some examples are rubber O-rings, threaded connections, precise machining to snug fitting, or some combination of the above. Preferably, intake valves 17, 51, and the bottom portion 39 are fitted using precise machining in connection with rubber O-rings. The burp baffle 71, 89, 103 is preferably fitted to the top using precise machining.

In accordance with the provisions of the patent statutes, the present invention has been described in what is considered to represent its preferred embodiment. However, it should be noted that the invention can be practiced otherwise than as specifically illustrated and described without departing from its spirit and scope.

What I claim is:

1. A gravity bolus feeding device, comprising:

a cylindrical body having a top and a bottom, said top and said bottom each being open, and defining a first fluid path in through said top and out through said bottom;

an intake valve disposed in said first fluid path to control the quantity of flow through said first fluid path;

a check valve having an intake disposed to receive fluids entering said cylindrical body from said bottom, and having an outtake disposed to pass fluids into said first fluid path before said intake valve, said check valve disposed between said top and said bottom and defining a second fluid path in from said intake of the check valve, through said check valve body, and out through said outtake of the check valve;

a burp baffle having a circular bottom section shaped to fit snugly within the open top of the cylindrical body, said bottom section having an opening near its outer circumference to allow fluid to pass from the container through or across said bottom section;

a center section connected to said bottom section nearer the top of the cylindrical body, said center section being an annular ring enclosing a hollow central cavity and further defining the inside wall of an annular cavity between said center section and the cylindrical body, said center section having an opening generally on the opposite side from said opening in said bottom section, said opening in said center section connecting said annular cavity with said hollow central cavity, said annular cavity being connected to said opening in said bottom section; and a top section connected to said center section opposite said bottom section, said top section covering the open top of the cylindrical body, said top section having a hole to allow air to pass through said top section out of the cylindrical body, said hole being connected to said hollow central cavity.

2. A gravity bolus feeding device, comprising:

a cylindrical body having a top and a bottom, said top and said bottom each being open, and defining a first fluid path in through said top and out through said bottom;

an intake valve disposed in said first fluid path to control the quantity of flow through said first fluid path;

a check valve having an intake disposed to receive fluids entering said cylindrical body from said bottom, and having an outtake disposed to pass fluids into said first fluid path before said intake valve, said check valve disposed between said top and said bottom and defining a second fluid path in from said intake of the check valve, through said check valve body, and out through said outtake of the check valve;

a burp baffle having a bottom section shaped to fit snugly within the open top of the cylindrical body, said bottom section having an opening near its outer periphery to allow fluid to pass from the fluid container through or across said bottom section;

a center section connected to said bottom section nearer the top of the cylindrical body, said center section being smaller in cross-section than the cylindrical body thereby defining a third fluid path within the cylindrical body and around said center section, said center section having an opening generally on the opposite side from said opening in said bottom section, said third fluid path being connected to both said opening in said center section and said opening in said bottom section; and a top section connected to said center section opposite said bottom section, said top section covering the open top of the cylindrical body, said top section having a hole to allow fluid to pass through said top section out of the cylindrical body, said hole being connected to said third fluid path by said opening in said center section.

3. A gravity bolus feeding device, comprising:

a cylindrical body having a top and a bottom, said top and said bottom each being open, and defining a first fluid path in through said top and out through said bottom;

an intake valve disposed in said first fluid path to control the quantity of flow through said first fluid path; and a check valve having an intake disposed to receive fluids entering said cylindrical body from said bottom, and having an outtake disposed to pass fluids into said first fluid path before said intake valve, said check valve disposed between said top and said bottom and defining a second fluid path in from said intake of the check valve, through said check valve body, and out through said outtake of the check valve.

4. A gravity bolus feeding device as described in claim 3, further comprising quantity markings on said cylindrical body.

5. A gravity bolus feeding device as described in claim 3, further comprising markings to indicate openness of said intake valve.

6. A gravity bolus feeding device as described in claim 3, further comprising a handle attached to said cylindrical body.

7. A gravity bolus feeding device as described in claim 6, wherein said handle is adjustable both up and down, and circumferentially around said cylindrical body.

8. A gravity bolus feeding device as described in claim 6, further comprising a hanger attached to said handle.

9. A gravity bolus feeding device as described in claim 7, further comprising a hanger attached to said handle.

10. A gravity bolus feeding device as described in claim 3, wherein said intake valve is completely closeable to prevent fluid from flowing along said first fluid path.

11. A gravity bolus feeding device as described in claim 3, wherein said check valve is a duck bill check valve.

12. A gravity bolus feeding device as described in claim 3, wherein said bottom is tapered.

13. A gravity bolus feeding device as described in claim 3, wherein said intake valve and said check valve are located on a removable bottom portion, said removable bottom portion cooperating with said cylindrical body to generally define a fluid chamber.

14. A gravity bolus feeding device as described in claim 13, wherein said intake valve and said check valve are removable from said removable bottom portion.

* * * * *